(12) United States Patent
Vanerek et al.

(10) Patent No.: US 9,610,379 B2
(45) Date of Patent: Apr. 4, 2017

(54) ABSORBENT FIBRES PRODUCED FROM LOW-SUBSTITUTED CARBOXYMETHYL CELLULOSE AND THE PROCESS THEREOF

(71) Applicant: FPINNOVATIONS, Pointe-Claire (CA)

(72) Inventors: Alois Vanerek, Montreal (CA); Jessica Carette, Salaberry-de-Valleyfield (CA); Zohreh Sabzalian, Montreal (CA); Theo Van De Ven, Montreal (CA); Md Nur Alam, Thunder Bay (CA)

(73) Assignee: FPINNOVATIONS, St-Jean, Pointe-Claire, Quebec (CA)

( * ) Notice: Subject to any disclaimer, the term of this patent is extended or adjusted under 35 U.S.C. 154(b) by 0 days.

(21) Appl. No.: 15/004,308

(22) Filed: Jan. 22, 2016

(65) Prior Publication Data

US 2016/0213804 A1    Jul. 28, 2016

Related U.S. Application Data

(60) Provisional application No. 62/106,829, filed on Jan. 23, 2015.

(51) Int. Cl.
| | |
|---|---|
| *B01J 20/32* | (2006.01) |
| *A61L 15/28* | (2006.01) |
| *B01J 20/24* | (2006.01) |
| *B01J 20/28* | (2006.01) |
| *B01J 20/30* | (2006.01) |

(52) U.S. Cl.
CPC ............... *A61L 15/28* (2013.01); *B01J 20/24* (2013.01); *B01J 20/28023* (2013.01); *B01J 20/3007* (2013.01); *B01J 20/3071* (2013.01); *B01J 20/3085* (2013.01)

(58) Field of Classification Search
CPC .................................. B01J 20/32; B01J 20/26
USPC ......................................................... 502/402
See application file for complete search history.

(56) References Cited

U.S. PATENT DOCUMENTS

| | | |
|---|---|---|
| 171,355 A | 12/1875 | Cottrell |
| 1,683,682 A | 9/1928 | Lilienfeld et al. |
| 1,683,831 A | 9/1928 | Lilienfeld et al. |
| 2,495,767 A | 1/1950 | Reid et al. |
| 2,619,483 A | 11/1952 | Wilcox et al. |
| 2,680,737 A | 6/1954 | Grassie et al. |
| 3,005,456 A | 10/1961 | Graham |
| 3,423,167 A | 1/1969 | Kuzmak et al. |
| 3,589,364 A | 6/1971 | Dean et al. |
| 3,678,031 A | 7/1972 | Schoggen |
| 3,723,413 A | 3/1973 | Chatterjee et al. |
| 4,068,068 A | 1/1978 | Holst et al. |
| 4,187,342 A | 2/1980 | Holst et al. |
| 4,199,367 A | 4/1980 | Smith |
| 4,248,595 A | 2/1981 | Lask et al. |
| 4,256,111 A | 3/1981 | Lassen |
| 4,289,824 A | 9/1981 | Smith |
| 6,080,420 A | 6/2000 | Qin et al. |
| 6,140,257 A | 10/2000 | Kershaw et al. |
| 6,548,730 B1 | 4/2003 | Patel et al. |
| 6,846,924 B1 | 1/2005 | Malmgren et al. |
| 7,229,689 B2 | 6/2007 | Qin et al. |
| 2008/0206293 A1 | 8/2008 | Toreki et al. |
| 2010/0144669 A1 | 6/2010 | Kernshaw et al. |
| 2012/0209234 A1 | 8/2012 | Bernt et al. |
| 2013/0012696 A1 | 1/2013 | Adden et al. |

FOREIGN PATENT DOCUMENTS

| | | |
|---|---|---|
| CA | 1062425 | 9/1979 |
| CA | 2100756 | 6/1996 |
| GB | 2220881 | 1/1990 |
| WO | 9312275 | 6/1993 |
| WO | 9416746 | 8/1994 |
| WO | 2004005595 | 1/2004 |

OTHER PUBLICATIONS

Dongmei Li at al., J. Appl. Polym. Sci., 117, 767-774 (2010).
International Search Report from corresponding PCT/CA2014/050559.

*Primary Examiner* — Edward Johnson
(74) *Attorney, Agent, or Firm* — Norton Rose Fulbright Canada LLP

(57) ABSTRACT

The invention relates to novel absorbent fibres/filaments from low-substituted carboxymethyl cellulose and the method of producing same. The filaments are produced by wet spinning, wherein the spinning dope is entirely comprised of low-substituted carboxymethyl cellulose dissolved in sodium hydroxide. The resulting CMC filaments have degree of substitution ranging from 0.10-0.35 and degree of polymerization ranging from 250-650 with the CMC uniformly distributed throughout the filament. The absorbency in deionized water and saline (0.9% NaCl) solution is 120 g/g and 30 g/g, respectively. The retention of deionized water and saline (0.9% NaCl) solution within the fibres is 48 g/g and 25 g/g, respectively.

19 Claims, 1 Drawing Sheet

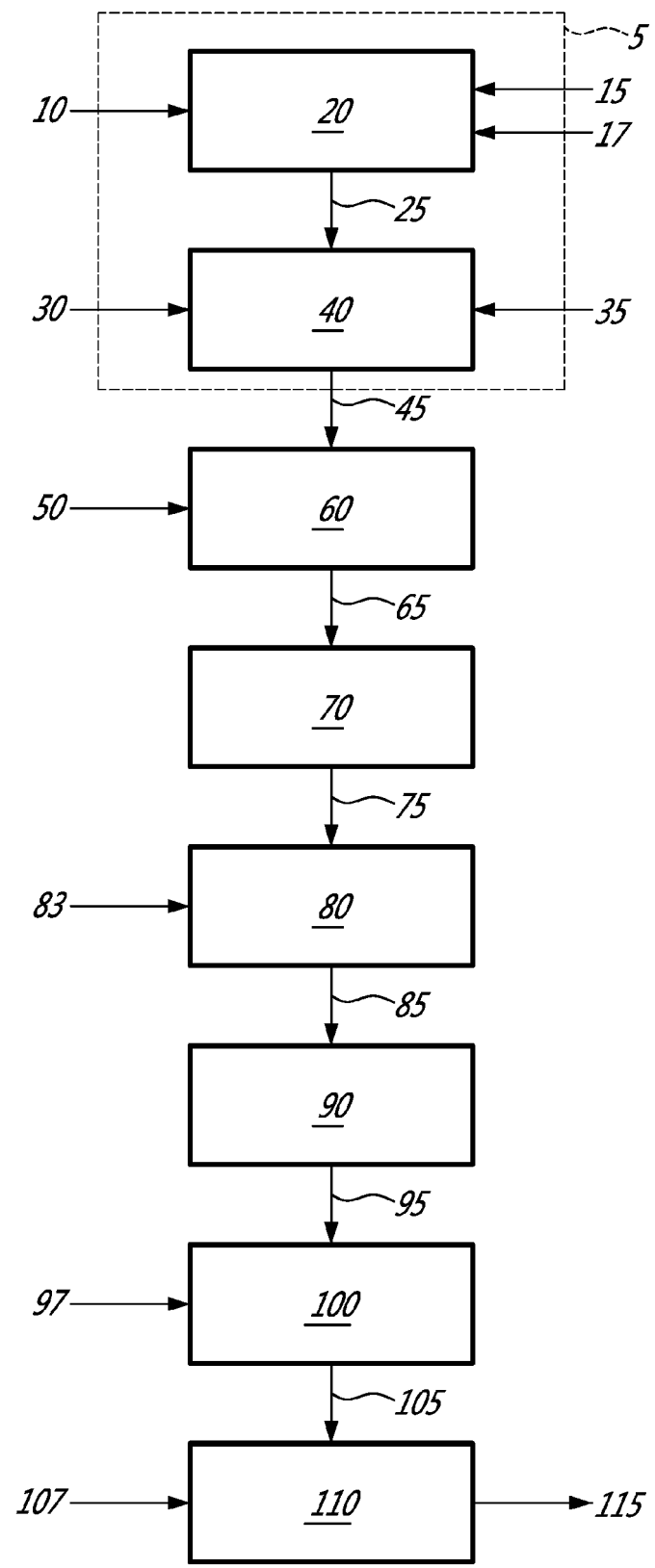

ABSORBENT FIBRES PRODUCED FROM LOW-SUBSTITUTED CARBOXYMETHYL CELLULOSE AND THE PROCESS THEREOF

BACKGROUND OF THE INVENTION i) Field of the Invention

The disclosed invention pertains to absorbent fibres made from regenerated low-substituted alkali metal carboxymethyl cellulose using a wet-spinning process. The fibres have high liquid absorption and high liquid retention capacities and are suitable for the use in wound dressing, absorbent hygiene products, wipes and medical applications.

ii) Description of the Prior Art

Absorbent polysaccharide fibres used in wound dressing, surgical dressing, surgical sponges, infant diapers, adult incontinence products, catamenial napkins, tampons, etc. are well known in the art. Polysaccharide fibres are derived from renewable resources and examples include: regenerated and non-regenerated cellulose fibres, chemically modified cellulose fibres, alginate fibres, chitosan fibres, pectin fibres, hyaluronic acid fibres and other fibres derived from polysaccharides or gums. Absorbent fibres and superabsorbents—materials capable of absorbing more than ten times their own weight of liquids, bodily fluids or blood—are used to enhance liquid absorbency as well as to ensure high liquid retention.

One polysaccharide used to a great extent to enhance liquid absorbency is sodium carboxymethyl cellulose (CMC). Besides being one of the most important cellulose derivatives, it is also relatively inexpensive. Carboxymethyl cellulose is chemically modified cellulose with the carboxymethyl group as a substituent. The carboxymethyl group contains a carboxyl group that can greatly improve the hydrophilic behaviour of cellulose. The properties and performance of carboxymethyl cellulose depend on the number of present carboxyl groups, i.e. the degree of substitution (DS).

Absorbent carboxymethyl cellulose fibres are highly desirable in hygiene and medical applications. However, the known processes for producing such fibres are complex and expensive: (i) spinning carboxymethyl cellulose fibres is difficult; (ii) carboxymethylation of regenerated or non-regenerated fibres incurs additional cost; (iii) carboxymethyl cellulose added into a spinning dope before fibres are made may slow down production; (iv) fibres from carboxymethyl cellulose having high DS are difficult to regenerate; and (v) fibres from carboxymethyl cellulose having low DS are difficult to process.

U.S. Pat. No. 2,495,767 describes continuous fibres spun from CMC having a DS between 0.5 and 1.0. The spinning dope contains 5% carboxymethyl cellulose and is extruded through a spinneret into a coagulation bath containing polyvalent metal cations such as copper, iron, lead, chromium, aluminium or their combination. The linear density of the spun fibres is between 72-566 dtex. Absorbent fibres can be also produced by extruding CMC solution through a spinneret into a coagulation bath that contains a water-miscible organic solvent and a cross-linker as suggested in U.S. Pat. No. 6,846,924. The patent claims that CMC with a DS below 0.35 has poor liquid absorption properties, and therefore, CMC having a DS above 0.35 is required. Water-miscible organic solvents, preferably alcohols, such as methanol, ethanol or isopropanol, or ketones, such as acetone, are used to regenerate fibres in the coagulation bath. Polyelectrolytes, such as polyvinyl amine and other quaternary polyamines or polyvalent metal cations, such as calcium, zirconium, magnesium, iron or aluminium, are used as cross-linking agents. The fibres are spun through jets with a diameter of 200 μm from a dope that contains between 7-12 CMC, depending on degree of polymerization. The saline (0.9% NaCl) absorption of the CMC fibres is 30 g/g.

Carboxymethyl cellulose is water soluble, however it can be cross-linked to obtain water-insoluble CMC. U.S. Pat. No. 3,589,364 relates to bibulous fibres produced by wet cross-linking of swollen regenerated or non-regenerated cellulose fibres with epichlorohydrin, followed by carboxymethylation. The degree of substitution is between 0.4-1.6, yet the carboxymethylated fibres are water-insoluble due to cross-linking. The total saline (0.9% NaCl) absorbency is between 4-12 g/g, while water absorbency is between 9-33 g/g. It is also possible to perform cross-linking and carboxymethylation at the same time as revealed in U.S. Pat. No. 4,068,068; U.S. Pat. No. 4,187,342; and U.S. Pat. No. 4,248,595.

CA Pat. No. 1,062,425 describes hydrophilic shaped structures of water-insoluble cellulose ethers that are capable of forming fibres or films. Hydroxyethyl cellulose, methyl-hydroxyethyl cellulose or carboxymethyl cellulose can be cross-linked to a low degree before its addition to a dope. The maximum attainable loading of pre-cross-linked CMC is 50% while the maximum water absorbency is 4.4 g/g. It is also possible to surface treat fibres or films during formation with pre-cross-linked cellulose ethers.

Besides cross-linking, CMC can be made substantially water insoluble by changing conditions during etherification reaction. U.S. Pat. No. 3,678,031 refers to substantially insoluble alkali metal carboxymethyl cellulose prepared with a molar excess of the neutralized etherifying agent, with extended reaction time from 3 hours to 24 hours and elevated temperature from 60° C. to 80° C. The substantially insoluble CMC has a DS between 0.4-1.2 and can absorb up to 70 times its own weight of aqueous solution. U.S. Pat. No. 3,723,413 describes water-insoluble carboxymethyl cellulose with a DS between 0.35 and 1.4 which is prepared by removing a portion of carboxymethylating reactants, residues and impurities formed during the reaction and then heat-treating the carboxymethyl cellulose. Based on the presented results, the calculated water absorbency of the resulting water-insoluble CMC is 6.2 g/g.

U.S. Pat. No. 4,256,111 describes a process where cellulose fibres, chemically modified by either phosphorylation or carboxymethylation, are refined to produce microfibrils. The suspension of microfibrillated cellulose is centrifuged to remove unbound water and the resultant viscous suspension of filament is then extruded in the form of continuous fibres using solvent exchange and subsequent drying. The fibre diameter is relatively large between 127-889 μm. Carboxymethylated fibres have total water absorbency between 40-50 g/g.

Polysaccharide fibres from the mixture of sodium alginate and sodium carboxymethyl cellulose can be regenerated in a coagulation bath containing a solution of calcium chloride as described in U.S. Pat. No. 7,229,689. The content of CMC is up to 15% and the dope is extruded through a 40,000-jet spinneret. The diameter of the jets is 70 μm. The fibres are carded and needled-punched to produce a non-woven fabric that absorbs around 21 g of saline (0.9% NaCl)/g fibre. In U.S. Pat. No. 6,080,420 the amount of carboxymethyl cellulose is increased to 30%. U.S. Pat. No. 6,140,257 relates to alginate/CMC fibres composed of at least of 10% alginate but less than 50% by weight. The remainder of the fibre composition is another polysaccharide, such as carboxymethyl cellulose, where the content of the other polysaccharide is between 40-90%. In addition, pectin could also be added from 0-20%. A 400-jet spinneret head is used to extrude the dope into a coagulation bath containing calcium chloride.

U.S. Pat. No. 20120209234 describes collapsible, hollow, rayon fibres that contained 5-50% CMC having a DS of 0.6-1.2. The absorbency of the resulting fibres is 5.2 g/g. The disadvantage of using CMC in rayon process is that the fibres tend to stick together due to gel formation at the surface of the fibres, and above 15% CMC content in the dope, the fibres do not float as conventional rayon fibres do, but sink which hinders production. U.S. Pat. No. 4,199,367 and U.S. Pat. No. 4,289,824 describe rayon staple fibres that contain 10-40% CMC having high fluid holding capacity. Carboxymethyl cellulose is added to viscose dope before the fibres are spun and the resulting alloy fibres have a maximum retention of 7 g/g. U.S. Pat. No. 3,423,167 relates to rayon fibres with a CMC content between 1-50% which have been subjected to wet-cross-linking. Cross-linking of swollen fibres in wet state leads to high water imbibition as opposed to cross-linking of dry collapsed fibres which have low liquid absorption capacity. U.S. Pat. No. 6,548,730 refers to carboxymethylation of regenerated cellulose fibres with sodium hydroxide and monochloroacetic acid. The carboxymethyl groups are believed to be predominantly in the amorphous regions and the degree of substitution is between 0.12-0.35.

WO Pat. No. 1993012275 describes solvent-spun fibres from tertiary N-oxide (referred to as Lyocell, also known as Tencel) that are carboxymethylated to obtain a DS between 0.2-0.5. The carboxymethylation is performed in a post-treatment of regenerated fibres with sodium hydroxide and monochloroacetate agent. The fibres are capable of absorbing 8-15 g saline (0.9 NaCl)/g fibres. Similarly, WO Pat. No. 1994016746 relates to wound dressing made of carboxymethyl cellulose fibres produced in the reaction of Lyocell/Tencel with sodium hydroxide and sodium monochloroacetate. The resulting fibres have a DS between 0.25-0.45 and absorbency of saline solution (0.9% NaCl) between 15-25 times their own weight.

U.S. Pat. No. 20100144669 describes preparation of fibres from carboxymethyl cellulose that was dissolved in an ionic liquid consisting of a tertiary amine N-oxide.

Hydroxyethyl cellulose (HEC) is a cellulose ether that is similar in behaviour to carboxymethyl cellulose. HEC can be spun using conventional rayon spinneret as described in Dongmei Li at al., J. Appl. Polym. Sci., 117, 767-774 (2010). Low-substituted HEC having a DS of 0.49 is dissolved in sodium hydroxide and then regenerated in a coagulation bath containing sulphuric acid, sodium sulphate and zinc sulphate. The HEC concentration is 7.6%, while NaOH concentration is 8%. The resulting HEC fibres have a titre of 1.67 dtex.

As seen from above, carboxymethylated fibres can be obtained by various methods including: (i) spinning CMC directly to a coagulation bath containing polyvalent ions as cross-linkers which may, or may not, also contain polyelectrolytes and organic solvents; (ii) admixing CMC to conventional rayon or Lyocell/Tencel fibres; (iii) co-spinning CMC with another polysaccharide such as alginate that is easier to regenerate; (iv) pre-cross-linking CMC prior to its addition to a dope containing other polysaccharides; (v) carboxymethylating conventional rayon or Lyocell/Tencel fibres; (vi) heat-treating CMC; (vii) spinning CMC from ionic liquids; and (viii) spinning microfibrillated carboxymethylated cellulose. In cases where carboxymethyl cellulose is used in a dope, the degree of substitution is above 0.35, preferably 0.4-1.2. In cases where regenerated or non-regenerated fibres are carboxymethylated, the degree of substitution is ranging from 0.12-0.5. In the post-treated fibres, carboxymethyl groups are likely to be located in the amorphous regions of the fibres and at or near the fibre surface because the carboxymethylation times are not long enough to permit even distribution of carboxymethyl groups inside the fibre. Alloy fibres spun from a dope containing high-substituted CMC consist of highly charged CMC molecules surrounded by underivatized, uncharged cellulose molecules, and may not be particularly absorbent.

SUMMARY OF THE INVENTION

The prior art does not teach spun fibres or filaments that can be obtained directly from a dope containing a low-substituted carboxymethyl cellulose as described herein. Spinning fibres/filaments directly from low-substituted carboxymethyl cellulose yields fibres with uniformly distributed charged carboxyl groups throughout the fibre/filament as well as at the surface. The low-substituted CMC cellulose molecules described herein, due to their uniform distribution throughout the filament, carry, on average, equal number of charged groups that promote high liquid absorbency and high liquid retention.

The present invention describes absorbent continuous fibres spun directly of low-substituted carboxymethyl cellulose and the method of producing same. The low-substituted CMC described herein has a DS between 0.10-0.35 and a degree of polymerization (DP) between 250-650. It is dissolved in sodium hydroxide, filtered and subsequently extruded in the form of filaments using a spinneret. The resulting spun fibres are washed with a mixture of water of pH 8 and organic solvent before being dried. The absorbency of the fibres is 120 g/g (from 20-150 g/g) in deionized water and 30 g/g (from 15 to 35 g/g) in a saline (0.9% NaCl) solution. The water retention of the fibres is 48 g/g (from 10 to 50 g/g) in deionized water and 25 g/g (from 10 to 30 g/g) in 0.9% NaCl solution.

In accordance with one aspect of the present invention, there is provided an absorbent continuous filament comprising: a carboxymethyl cellulose uniformly distributed throughout the filament, the filament having a degree of substitution (DS) of 0.10 to 0.35 and a degree of polymerization (DP) of 250 to 650.

In accordance with another aspect of the filament herein described, comprising: a titre of 0.5 to 20 dtex; and a tenacity of 0.5 to 2.5 cN/dtex.

In accordance with yet another aspect of the filament herein described, comprising: a water absorbency 20-150 g/g; and a saline (0.9% NaCl) absorbency of 15 to 35 g/g.

In accordance with still another aspect of the filament herein described, comprising: a water retention from 10 to 50 g/g; and a saline (0.9% NaCl) retention of 10-30 g/g.

In accordance with yet still another aspect of the filament herein described, the filament is formed from low-substituted sodium carboxymethyl cellulose.

In accordance with a further aspect of the filament herein described, the DS is 0.15 to 0.27.

In accordance with yet a further aspect of the filament herein described, the DP is 350 to 450.

In accordance with still a further aspect of the present invention, there is provided a method for producing a spun, continuous, absorbent filament, the method comprising the steps of: mercerising and depolymerising a cellulose; carboxymethylating the cellulose to produce carboxymethyl cellulose having a degree of substitution of 0.10 to 0.35;

depolymerising the carboxymethyl cellulose to a degree of polymerisation of 250 to 650; washing the carboxymethyl methyl cellulose with a mixture of water and alcohol to remove bi-products of reactions; drying the carboxymethyl cellulose to produce a source carboxymethyl cellulose; dissolving the source carboxymethyl cellulose in an alkali metal hydroxide to produce a dope; removing undissolved solids from the dope to produce a clarified dope; extruding the clarified dope through a spinneret; and regenerating the carboxymethyl cellulose in an acid-containing bath via a hydrogen bonding-mechanism as the continuous spun absorbent filament.

In accordance with yet still a further aspect of the method herein described, further comprising washing the continuous spun absorbent filament with a mixture of water and alcohol to remove acid and its salt and adjusting pH of the continuous spun absorbent filament to a pH between 7 to 8 before drying.

In accordance with an embodiment of the method herein described, the cellulose originates from a non-regenerated cellulosic fibre.

In accordance with another embodiment of the method herein described, the carboxymethylating the cellulose is in a medium comprising a water content of 10 to 40 w/w %.

In accordance with yet another embodiment of the method herein described, wherein the method of depolymerising of the cellulose is in a reaction with oxidizing agents under alkaline conditions.

In accordance with still another embodiment of the method herein described, the oxidizing agents are hydrogen peroxide, sodium hypochlorite or oxygen.

In accordance with yet still another embodiment of the method herein described, the depolymerising of the cellulose occurs after carboxymethylation.

In accordance with a further embodiment of the method herein described, the depolymerising of the cellulose occurs before carboxymethylation.

In accordance with yet a further embodiment of the method herein described, the water content is 15 to 30 w/w %.

In accordance with still a further embodiment of the method herein described, the DS is 0.15 to 0.27.

In accordance with yet still a further embodiment of the method herein described, the DP is 350 to 450.

In accordance with still a further embodiment of the method herein described, the filament is formed from low-substituted hydrogenated and/or sodium carboxymethyl cellulose.

BRIEF DESCRIPTION OF THE DRAWING

FIG. 1 is a block diagram of a method of producing an absorbent filament from low-substituted carboxymethyl cellulose in accordance with one embodiment described herein.

DETAILED DESCRIPTION OF THE INVENTION

Carboxymethyl cellulose, viscose rayon, Lyocell/Tencel or cuprammonium rayon are exclusively produced from cotton, dissolving pulp or pre-hydrolyzed kraft pulp, all of which have a high α-cellulose content. Absorbent filaments from low-substituted CMC, in addition to those cellulose substrates above, can be made from conventional kraft pulp, hardwood or softwood, which contains about 20% by weight of other polysaccharides than cellulose. These polysaccharides, also referred to as hemicelluloses, are often branched and carboxylated which is beneficial to liquid absorbency of the final spun fibres. The preferred feed stock for the present invention is derived from conventional kraft pulp, that is substantially, at least 80% by weight of cellulose and less than 5% lignin.

DEFINITIONS

The term fibre and filament are used herein interchangeably and described here is a shaped, filamentous object. A continuous fibre/filament is understood to have a very long length.

High α-cellulose is understood at over 90 w/w % cellulose that will not dissolve in 17.5 w/w % NaOH.

Mercerization is a process of treating the cellulose substrate with a sodium hydroxide solution at a concentration equal to or above 17 w/w %. During mercerization, cellulose is converted to a sodium form, commonly referred to as alkali cellulose or sodium cellulosate, which is much more reactive than the native cellulose. The presence of sodium hydroxide also causes depolymerisation of cellulose chains.

Degree of substitution (DS) is a measure of how many of the three (3) hydroxyl groups (—OH) of the anhydroglucose units (AGU) have been substituted for carboxymethyl groups. The maximum DS value is three (3). For the present invention, the DS is between 0.10 to 0.35 which means that CMC swells in water, but is water insoluble. In a cellulose chain, each AGU (having 3-OH groups) is on average substituted with between 0.10 and 0.35 carboxymethyl groups. A carboxymethyl cellulose having this range of DS is understood to mean a low-substituted CMC. The degree of substitution was determined using ASTM-D1439-03 (2008).

The water content during carboxymethylation is understood as the mass of water related to the total mass of added liquids, water and ethanol. The optimum water content to produce low-substituted carboxymethyl cellulose that readily dissolves in sodium hydroxide to produce a spinning dope is 10-40 w/w %. Below and above this range, cellulose carboxymethylation is not sufficiently homogeneous to produce low-substituted carboxymethyl cellulose that fully dissolves in sodium hydroxide and the resultant undissolved solids interfere with the production of the clarified dope during the filtration purification process.

Degree of polymerisation (DP) is understood as the number of anhydroglucose units in the cellulose macromolecule. For the present invention, the DP is between 250 to 650, that is the CMC of the present invention has from 250 to 650 AGU. For the present CMC, only between 75 and 260 of these sites per cellulose chain have been substituted with carboxymethyl groups. The degree of polymerisation was calculated from viscosity using SCAN-C15 (1962).

Depolymerisation of cellulose is performed under alkaline conditions before or after carboxymethylation. Oxidizing agents such hydrogen peroxide, sodium hypochlorite or oxygen cause cleavage of cellulose chains, thus reducing the degree of polymerization. Oxygen or air can be pressurized to increase the reaction rate of cellulose depolymerisation.

After the carboxymethylation reaction and cellulose depolymerisation, low-substituted carboxymethyl cellulose is washed several times with a mixture of water and alcohol to remove bi-products such as sodium chloride and sodium glycolate. A typical water to alcohol ratio would be 30:70 by volume. The degree of washing depends on the purity of the source carboxymethyl cellulose which should be greater than 90 w/w %, preferably greater than 95 w/w %. The last washing is performed with alcohol only before the source carboxymethyl cellulose is dried.

The expression "CMC uniformly distributed throughout the filament" is defined herein as CMC groups that are found evenly/uniformly distributed from the centre of the filament to the surface of the CMC filament. This is in contrast to post-treated CMC filaments where CMC is most likely substituted only on or near the surface of the filament. As previously stated, swelling of the CMC filament occurs upon contact with water. The extent of swelling (120 g/g) is an indirect measure of the uniformity of the distribution of carboxymethyl within the cellulose.

It should also be noted that for the present invention, the hydroxyl groups of the anhydroglucose units are only substituted with sodium form of carboxymethyl groups and no other groups are necessary to further derivatize the carboxymethyl cellulose.

The titre, expressed in "dtex", is a unit of linear mass density of fibres that is specifically established as the mass in grams per 10,000 meters.

Tenacity is a measure of the filament strength and is expressed in terms force per linear mass density (cN/dtex).

Elongation is a measure of increasing fibre length under a given extension rate and is expressed as a percentage increase from the initial length under no load.

Water absorbency is defined as grams of water absorbed per gram of filament after 24 hrs using a free swelling technique.

Similarly, saline (0.9% NaCl) absorbency is measured in terms of grams of the saline solution per gram of filament after 24 hrs using a free swelling technique.

Water and saline (0.9% NaCl) retention is established in terms of grams of liquid per gram filament after subjecting the filament to force which removes unbound water from the filament. To determine the liquid retention, 1 gram of fibres from the free-swelling experiments was subjected to a force of 900 g in a centrifuge for a period of 30 minutes (Tappi Useful Method UM256).

Referring to FIG. 1, the carboxymethylation reaction 5 is carried out by a two-step process. The starting material is non-regenerated cellulosic fibre 10 milled to ensure cellulose accessibility to chemicals in the ensuing reaction. The milled cellulosic fibres 10 (20 g) were suspended in a mixture 15 of 15 g water and 160 g ethanol. The concentration of water in the liquid phase was between 10-40 w/w %, preferably between 15-30 w/w %. Sodium hydroxide 17 (30 g) at a concentration of 50 w/w % by weight was added and mercerization 20 was allowed to proceed for 30 minutes at a temperature of 65° C., depolymerisation also takes place during mercerisation. Product of mercerization is alkali cellulose 25. After mercerization 20 process was completed, monochloroacetic acid 30 at a concentration of 80% was added. The amount of monochloroacetic acid 30 was such as to reach a DS between 0.10-0.35, preferably between 0.15-0.27. The reaction between the mercerized cellulose 25 and monochloroacetic acid 30 was allowed to proceed for 1 hour at a temperature of 65° C.

At the end of the reaction, oxygen 35 was introduced at a pressure of 100 psi for a period of 7-10 minutes. If compressed air is used, the time required to depolymerize cellulose is (5) times longer due to a lower oxygen concentration in air. The present process adds only carboxymethyl group onto the cellulose and is substantially free of another cellulose derivatization. Oxygen causes cellulose degradation/depolymerisation 40, i.e., reduction in DP. The desired DP for the low-substituted CMC 45 was between 250-650, preferably between 350-450, which ensured up to 97% dissolution of resulting carboxymethyl cellulose in sodium hydroxide 83. In addition to oxygen, DP can be reduced by other oxidizing agents such as hydrogen peroxide or sodium hypochlorite. Adding different oxidizing agents may necessitate adjustments in the amount of NaOH required. After the depolymerisation 40 was completed, pressure was released and the carboxymethylated cellulose was washed 60 with the mixture 50 of water and alcohol (70:30), then the CMC 65 was steeped with anhydrous alcohol (≥99.5 v/v %) before drying 70.

Washed, dried, low-substituted CMC 75 having a DS of 0.10-0.35, preferably between 0.15-0.27, and a DP of 250-650, preferably between 350-450, was dissolved 80 in sodium hydroxide 83 to form a viscous liquid called a spinning dope 85. The concentration of NaOH ranged between 3-10 w/w %, preferably between 5-8 w/w % and the CMC concentration varied from 4-12 w/w %, preferably 7-9 w/w %. The dope 85 was filtered and then transferred to a feed reservoir of a wet-spinning machine 90. A rayon spinneret is a suitable wet-spinning equipment 90 to be used for the production of fibres from low-substituted CMC. The dope 85 was degassed before it was extruded into a coagulation bath 100 that contained an acid. Acids, in particular, strong acids 97 regenerate the low-substituted CMC in the form of fibres/filaments 105. The most suitable strong acids are sulphuric acid and hydrochloric acid. Typical concentrations of sulphuric acid ranged from 5-20 w/w %, preferably 10-15 w/w %, but in some cases the concentration could be increased beyond 20 w/w %.

Low-substituted CMC 75 dissolves in NaOH 83 due to electrostatic repulsion of the carboxyl groups. In the presence of NaOH, the electrostatic repulsive forces overcome hydrogen bonding that holds cellulose molecules together and, as a result, CMC dissolves forming a spinning dope 85. During wet spinning 90, the dope from low-substituted CMC was extruded 95 through jets of the spinneret head which were submerged in an acidic bath 100. The jet opening was 70 µm and a the spinneret plate contained 3,000 jets. In contact with a strong acid 97, NaOH is neutralized, forming a salt of the respective acid. The sudden drop in pH leads to reduction of the electrostatic repulsive forces and reinstitution of hydrogen bonding which in turns leads to regeneration of low-substituted CMC in the form of fibres 105. Low-substituted CMC contains limited number of carboxyl groups and therefore a large portion remains in the form of unmodified cellulose which participates in intermolecular hydrogen bonding, thus leading to filament formation.

The low-substituted carboxymethyl cellulose of the present application is soluble in NaOH and regenerates readily due to a large number of hydrogen bonding domains. This is believed to be one of the reasons, why the CMC of the present application requires a DS in the range of 0.10 to 0.35. This range of DS combined with DP 250-600 gives the CMC described herein the ability to: a) dissolve in alkali metal hydroxides and b) regenerate as CMC fibres in acids. This is in contrast to a high-substituted CMC which is water soluble but due to the presence of a high number of charged groups which interfere with the hydrogen bonding does not readily regenerate. The hydrogen bonding alone is sufficient, but it is not restricted to regenerating low-substituted CMC fibres without the necessity of using polyvalent metal cations, cross-linkers, polyelectrolytes, heat treatment or organic solvents.

The regenerated spun fibres 105 undergo stretching, washing, finishing treatment and drying 110. Washing of the spun fibres is performed in a mixture 107 of water and an organic solvent to prevent excessive swelling of fibres. Sodium hydroxide is added to water to ensure that pH of the spun fibres 115 is between 7-9. Short-chain alcohols such as methanol, ethanol or isopropanol, or ketones such as acetone, are suitable for washing. The volume ratio of water to organic solvent mixture 107 can vary, depending on DS. At lower DS less organic solvent is required than at higher DS. A typical volume ratio of water to solvent would be 30:70 for fibres having a DS between 0.15 and 0.27. Alternatively, it is possible to wash the spun fibres with water having a pH below 4 which considerably reduces the filament swelling. Surface active agents that reduce surface tension of the washing liquid can also be utilized during the washing and/or finishing stages. The last washing/finishing stage consists of pure organic solvent that replaces most of water in the fibres before drying thus reducing brittleness.

Example 1

An amount of 9.21 g of air-dried, low-substituted carboxymethyl cellulose, having a degree of substitution of 0.25 and a degree of polymerization of 450, was added to a mixture of 90.5 mL of water and 12.4 g of sodium hydroxide 50 w/w % solution contained in 500 mL steel vessel and pre-cooled to 15° C. The suspension was stirred until the low-substituted carboxymethyl cellulose dissolved. The resulting dope was 8.3% carboxymethyl cellulose and 6% sodium hydroxide. The dope was centrifuged to remove un-dissolved particles and the dissolution rate of was found to be 97 v/v %. The dope was then extruded with a syringe equipped with a needle of gage from 20 to 25 at constant injection speed of 5 mL/min via syringe pump into a 10% sulphuric acid. The formed filament was rinsed with deionized water and air dried under tension. The titre varied from 120 to 200 dtex with a tenacity ranging from 0.45 to 1.10 cN/dtex, elongation ranging from 6 to 17% and water absorbency between 0.2 to 3.8 g/g.

Example 2

An amount of 1.0 kg of low-substituted carboxymethyl cellulose, having a degree of substitution of 0.27 and a degree of polymerization of 450, was added to a solution containing 1,500 g of 50 w/w % sodium hydroxide and 11,750 mL of water to form a 8 w/w % cellulose solution in 6 w/w % caustic by weight. A high-shear mixer was used to facilitate the dissolution of cellulose at a temperature of 15° C. The dope was filtered through 20 μm filter to remove un-dissolved particles larger than ⅓ the spinneret jet opening (60 μm). The dope was then extruded through a pilot 3,000-jet rayon spinneret into a coagulation bath containing 13 w/w % sulphuric acid, 25 w/w % sodium sulphate and 5 w/w % zinc sulphate at 50° C. The multi-filament tow was spun at a draw-off speed of 10-50 m/min and a stretch 10-30%. The spun fibres were washed first with 10% sulphuric acid and then hot water. In the next washing stage, the spun fibres were washed with a mixture of water and ethanol (30:70 by volume). The pH of water prior to its addition to ethanol was adjusted to a pH of 8. The fibres were rinsed in a final bath of acetone before being dried with forced hot air. The resulting fibres had a titre of 1.3-3.3 dtex, a tenacity of 0.78-1.43 cN/dtex, a stretch of 15-37%, a water absorbency of 120 g/g, a saline (0.9% NaCl) absorbency of 30 g/g, a water retention of 48 g/g and a saline (0.9% NaCl) retention of 25 g/g.

The invention claimed is:
1. An absorbent continuous filament comprising:
   a carboxymethyl cellulose uniformly distributed throughout the filament, the filament having a degree of substitution (DS) of 0.10 to 0.35 and a degree of polymerization (DP) of 250 to 650.
2. The filament of claim 1, comprising a titre of 0.5 to 20 dtex, and a tenacity of 0.5 to 2.5 cN/dtex.
3. The filament of claim 1, comprising a water absorbency 20 to 150 g/g, and a saline (0.9% NaCl) absorbency of 15 to 35 g/g.
4. The filament of claim 1, comprising a water retention from 10 to 50 g/g, and a saline (0.9% NaCl) retention of 10 to 30 g/g.
5. The filament of claim 1, wherein the filament is formed from low-substituted sodium carboxymethyl cellulose.
6. The filament of claim 1, wherein the DS is 0.15 to 0.27.
7. The filament of claim 1, wherein the DP is 350 to 450.
8. A method for producing a spun continuous absorbent filament, the method comprising the steps of:
   mercerising and depolymerising a cellulose;
   carboxymethylating the cellulose to produce carboxymethyl cellulose having a degree of substitution of 0.10 to 0.35;
   depolymerising the carboxymethyl cellulose to a degree of polymerisation of 250 to 650;
   washing the carboxymethyl methyl cellulose with a mixture of water and alcohol to remove bi-products of reactions;
   drying the carboxymethyl cellulose to produce a source carboxymethyl cellulose;
   dissolving the source carboxymethyl cellulose in an alkali metal hydroxide to produce a dope;
   removing undissolved solids from the dope to produce a clarified dope;
   extruding the clarified dope through a spinneret; and
   regenerating the carboxymethyl cellulose in an acid-containing bath via a hydrogen bonding-mechanism as the continuous spun absorbent filament.
9. The method of claim 8, further comprising washing the continuous spun absorbent filament with a mixture of water and alcohol to remove acid and its salt and adjusting pH of the continuous spun absorbent filament to a pH between 7 to 8 before drying.
10. The method of claim 8, wherein the cellulose originates from a non-regenerated cellulosic fibre.
11. The method of claim 8, wherein the carboxymethylating the cellulose is in a medium comprising a water content of 10 to 40 w/w %.
12. The method of claim 8, wherein the method of depolymerising of the cellulose is in a reaction with oxidizing agents under alkaline conditions.
13. The method of claim 11, wherein the oxidizing agents are hydrogen peroxide, sodium hypochlorite or oxygen.
14. The method of claim 11, wherein the depolymerising of the cellulose occurs after carboxymethylation.
15. The method of claim 11, wherein the depolymerising of the cellulose occurs before carboxymethylation.
16. The method of claim 11, wherein the water content is 15 to 30 w/w %.
17. The method of claim 8, wherein the DS is 0.15 to 0.27.
18. The method of claim 8, wherein the DP is 350 to 450.
19. The method of claim 8, wherein the filament is formed from low-substituted hydrogenated and/or sodium carboxymethyl cellulose.

* * * * *